United States Patent [19]

Bornat et al.

[11] 4,345,414

[45] Aug. 24, 1982

[54] SHAPING PROCESS

[75] Inventors: Alan Bornat; Roy M. Clarke, both of Liverpool, England

[73] Assignees: Imperial Chemical Industries Limited, London; University of Liverpool, Liverpool, both of England

[21] Appl. No.: 94,799

[22] Filed: Nov. 15, 1979

[30] Foreign Application Priority Data

Nov. 20, 1978 [GB] United Kingdom ............... 45297/78

[51] Int. Cl.³ ............................................. B29C 25/00
[52] U.S. Cl. ............................................. 53/425; 3/1;
3/1.4; 206/363; 264/24; 264/234; 264/235
[58] Field of Search ................. 264/24, 230, 234, 235;
53/425; 3/1, 1.4; 206/363

[56] References Cited

U.S. PATENT DOCUMENTS 4,043,331  8/1977  Martin .............................. 264/24 X
4,223,101  9/1980  Fine .................................. 264/24 X Primary Examiner—Thomas P. Pavelko
Attorney, Agent, or Firm—Cushman, Darby & Cushman

[57] ABSTRACT

A process for setting in a desired shape a product at least a portion of which comprises electrostatically spun fibres is disclosed. The process comprises maintaining the product in the desired shape at a temperature below the melding temperature of the electrostatically spun fibres. The desired shape may be the as-spun shape of the product or a shape obtained by deformation of the product, i.e. the product is reshaped. The fibres preferably comprise a polyurethane and reshaping is preferably effected on a former. The reshaped product may be employed as a vascular prosthesis.

24 Claims, 6 Drawing Figures

SHAPING PROCESS

This invention relates to a process for setting a product in a desired shape and particularly to a process for setting in a desired shape a product at least a portion of which comprises electrostatically spun fibres.

The technique of electrostatic spinning of liquids including solutions containing a fibre-forming material, is known and has been described in a number of patents as well as in the general literature.

The process of electrostatic spinning involves the introduction of a liquid into an electric field, whereby the liquid is caused to produce fibres which tend to be drawn to a charged receiver. While being drawn from the liquid the fibres usually harden, which may involve mere cooling (where the liquid is normally solid at room temperature, for example), chemical hardening (for example by treatment with a hardening vapour) or evaporation of solvent (where this is present). The product fibres may be collected on the suitably located charged receiver and subsequently stripped therefrom, or, where the receiver is a product the surface of which is to be rendered fibrous, retained in contact therewith.

The fibres obtained by the electrostatic spinning process are thin, and for the purposes of the present invention they are usually of the order of 0.1 to 25 micron, preferably 0.5 to 10 micron, more preferably 1.0 to 5 micron and particularly preferably 1 micron ±20% in diameter.

The fibres, if collected to form a mat of appropriate thickness may, because of the inherent porosity of the mat so obtained, provide a product having a wide variety of applications, depending upon the composition of the fibres, their density of deposition, their diameter, and their inherent strength and the thickness and shape of the mat. It is also possible to post-treat such mats with other materials to modify their properties, for example to increase their strength or water resistance.

Products having different properties may be obtained by adjusting their composition for example, by electrostatically spinning a liquid containing a plurality of components, each of which may contribute a desired characteristic to the finished product, or by simultaneously spinning from different liquid sources fibres of different composition which are simultaneously deposited to form a layer having an intimately intermingled mass of fibres of different material. A further method is to produce a product having a plurality of layers of different fibres (or fibres of the same material but with different characteristics, e.g. diameter) deposited, say, by varying with time the fibres being deposited upon the receiving surface. One way of effecting such a variation, for example, would be to have a moving receiver passing in succession sets of spinnerets from which fibres are being electrostatically spun, said fibres being deposited in succession as the receiver reaches an appropriate location relative to the spinnerets. Furthermore, the electric field about the charged receiver may be modified to alter the pattern in which the fibres are deposited on the charged receiver, and hence the mechanical properties of the product, as described in our copending British patent application No. 40029/78.

Applications in which products comprising electrostatically spun fibres may be employed include inter alia medical products, e.g. wound dressings, prosthetic devices, and industrial products, e.g. electrolytic cell diaphragms, battery separators, fuel cell components. For example our German patent application No. OLS 2704771 describes inter alia the production of tubular fibrous products or products comprising a tubular portion, using the technique of electrostatic spinning, and particularly the electrostatic spinning of fibre-forming compositions comprising a polyurethane, so that tubular products comprising polyurethane fibres having the above mentioned dimensions are obtained. Preferably substantially all of the electrostatically spun fibres of the product are of polyurethane material. One example of such a tubular product is a vascular prosthesis, particularly a synthetic blood vessel. Other applications for such tubular products include use as ducts of a variety of kinds, e.g. urinary and bile as well as tubular components of structures of other configuration, for example, heart components and components of auxiliary medical equipment, particularly where contact, especially lengthy contact, with living tissue is envisaged. Such tubular products are particularly valuable where intermittent stretching or swelling of the product, such as may result from pulsed flow of liquid therethrough, is likely to occur.

We have now found that a product at least a portion of which comprises electrostatically spun fibres may be set in a desired shape and/or size by maintaining at least a portion of the said product at a temperature between the melding temperature of the fibres and room temperature and then cooling the product.

By "set" we mean that the product retains substantially all of the desired shape/size during its useful life.

By "melding temperature" we mean the temperature at which the fibres start to flow or, where they do not flow, the temperature at which they sinter, or where they do not flow or sinter, the temperature at which they decompose. Conveniently a sample of a product comprising electrostatically spun fibres may, after heat treatment be examined under a scanning electron microscope to determine whether melding of the said fibres has occurred.

Accordingly the present invention provides a process for setting a product at least a portion of which comprises electrostatically spun fibres which process comprises maintaining the product in a desired shape/size at a temperature between the melding temperature of the fibres and room temperature and then cooling the product or allowing it to cool.

While the desired shape may be that in which the product was spun, often the desired shape is different to that in which the product was spun, i.e. the product is reshaped. Where the product is reshaped in the process of the present invention it is often necessary to hold the product under stress in the reshaped form until it is set.

Accordingly a further aspect of the invention provides a process for reshaping a product at least a portion of which comprises electrostatically spun fibres which process comprises the steps of deforming the product to give the product a desired shape and setting the product in the said shape as hereinbefore described.

Normally the product will be set as a continuation of the manufacturing process and then stored for use but it may also be set (a) on location, e.g. in hospital where it may be matched to an existing component or to a location or (b) in situ where it is to be used.

Preferably the temperature at which the product is maintained during the process of the present invention is between 60° C. and 5° C. below the melding temperature of the fibres and more preferably between 30° C. and 15° C. below the melding temperature of the fibres.

For example, where the fibres comprise a polyurethane, e.g. a polyurethane prepared from polytetrahydrofuran, butanediol, and methylene-di-isocyanate molar ratio 1:2.25:3.3) having a melding temperature of 105° C., the product is typically maintained at a temperature in the range 75° C. to 90° C.

Where the product comprises a plurality of fibres of different melding temperature, the temperature at which the product is maintained during the process of the present invention is often lower than the lower or lowest melding temperature of the fibres of which the product is composed if these are present in sufficient amount to determine the temperature at which the product can be set.

Where a product is reshaped by the process of the present invention the stress to which the product is subjected during the temperature-maintaining step is often sufficient to alter the size of the product.

Generally the product is released after being set but we do not exclude the possibility that it may be held permanently in the desired shape, e.g. where it is set in situ where it is to be used. Where the product is released after being set the temperature at which it is released depends inter alia on the composition of the fibres. Conveniently the temperature of the product is lowered to room temperature before the product is released.

The period of time over which the product is maintained at an elevated temperature in the process of the present invention is sufficiently long such that the product retains substantially the whole of the desired shape/size during its useful lifetime. Typically the said period of time is between 12 and 48 hours and where a tube, e.g. of a polyurethane, having a wall thickness of about 0.5 mm is set by the process of the present invention, about 24 to 36 hours is often preferred. However, it will be appreciated that the said period of time may depend inter alia on the temperature at which the product is maintained, and the structure and composition thereof.

Where a product is reshaped by the process of the present invention it will be appreciated that sufficient material is preferably present in the product prior to reshaping to allow the product to be reshaped with substantially no destruction of its structure occurring. However, we do not exclude the possibility that it may be desired to alter the structure of the product slightly.

Where a product is reshaped by the process of the present invention small or surface irregularities are often introduced into the product during the deformation step. However, we have found that where there is a tendency to introduce irregularities into the product during the deformation step these may be removed by applying a stress to the product to remove the irregularities prior to the temperature-maintaining step of the present process and retaining the stress during the said temperature-maintaining step. For example, where a straight tube comprising electrostatically spun fibres is deformed in the absence of a longitudinal stress to form an arc of a circle creases may be formed in the wall of the tube which forms the arc of the circle of smaller radius and the bend may be so severe that the tube kinks and even collapses. However, where such creases and/or kinks are removed by the application of stress to the products prior to and during the said temperature-maintaining step, crease-free and kink-free products may be obtained.

While the stress, where it is employed, may be tensile or compressive, it is often more convenient, particularly where the product has one dimension at least an order of magnitude less than the other two, to apply a tensile stress to the product.

The degree of stress to which the product, or the proportion thereof comprising electrostatically spun fibres, is subjected in the process according to the present invention is often sufficient to effect a strain (the ratio, expressed as a percentage, of the change in a dimension of the product when subjected to the said stress to the unstressed dimension) in the product, or in the said portion thereof of less than 25%, typically about 20%. Preferably the product is not stretched beyond its elastic limit.

It is often preferred that the product is mounted on, and preferably attached to, a former prior to subjecting it to a temperature-maintaining step of the present process. However, we do not exclude the possibility that the product, where it is reshaped, is reshaped in the absence of a former, e.g. a product having a non-planar shape may be held at a plurality of points and subjected under stress to a suitable holding step to give it a planar shape.

By "former" we mean a structure on which the product at least a portion of which comprises electrostatically spun fibres is mounted and which imparts to the product a desired shape.

Where a former is employed it may have the desired shape before the product is mounted thereon or it may be deformed to give the desired shape after the product has been mounted thereon.

Where a former is employed it may be made of metal, plastics, wood, glass or any other material or combination thereof which will withstand the stress, where stress is employed in the process of the present invention, and the conditions e.g. temperature, of the holding step. It will be appreciated that a former, where it is employed, is contactable physically with at least a proportion of the product and preferably removable therefrom after the shape of the product has been changed. However, we have found that it is often convenient to retain the reshaped product on the former, at least temporarily, e.g. during storage and/or transportation, to reduce the possibility of the reshaped product being damaged. Moreover we do not exclude the possibility that the former may be retained permanently in contact with the product.

Where the electrostatically spun product is in the form of a tube, the former, particularly where the lumen of the tube is small, or where the tube is particularly long or thin-walled and fragile, preferably consists of a core and a sheath of suitable material, the core serving to maintain the configuration of the sheath.

The core is conveniently a mandrel of substantially cylindrical configuration and of diameter approximating to the internal diameter of the sheath. The core preferably has a smooth surface to facilitate sliding of the sheath upon the core when the core is located therein, and when it is removed therefrom. The core is conveniently a metal rod or wire, preferably a copper wire.

The sheath preferably comprises a polymeric material, although the use of a sheath made of metal foil or fibrous material, is not excluded. Most preferably the sheath will have such a thickness and be of such a construction that it can easily be deformed and at least partially coolapsed so that it is capable of being withdrawn conveniently from the lumen of a tube which has been reshaped. We do not exclude the possibility, however, that the sheath comprises localised thickening or contouring as may be required for example to impart a desired contour or a particular configuration to the product. For example it may be desirable for the sheath to have rigid ends, which may facilitate its handling and which can be detached, e.g. by cutting, before collapsing the sheath to remove the tubular product. It is sometimes advantageous to coat one or both surfaces of the sheath to facilitate its removal from the core and/or tubular product.

The major part of the sheath, then, should be deformable, preferably collapsible and more preferably it will comprise a thermoplastics or rubber material conveniently of thickness between 0.1 mm and 5 mm preferably between 0.2 mm and 2 mm and more preferably between 0.5 mm and 1 mm. Although it will be appreciated that the thickness of the sheath will depend inter alia on the inner diameter of the electrostatically spun tube and on the diameter of the core. Most thermoplastics are suitable provided of course, that they are able to withstand the conditions to which they are subjected during the process of the present invention, that they do not react undesirably with any material which they contact in the course of the process of the invention, e.g. solvent from which the fibres may have been spun, and that they do not tend easily to contaminate the product undesirably, e.g. with plasticiser residues. Examples of suitable sheaths include plastics and rubber tubes e.g. silicon rubber and thermoplastic helices of the sort often used as electrical insulation on a metal conductor. Such a helix can be temporarily stretched to reduce its diameter while it is being inserted in and removed from an electrostatically spun tube. Typical thermoplastics from which such helices are prepared include polyethylene, polypropylene, polytetrafluoroethylene and nylons. Where the sheath comprises a tube it is often convenient to employ an extensible tube, e.g. a tube made of a suitable rubber, typically a silicone rubber, and preferably a rubber tube having an external diameter smaller than that of the internal diameter of the product to be reshaped since such a tube facilitates the said mounting and deforming steps, for example where the product comprises a polyurethane tube of internal diameter 6 mm, it is often convenient to employ as a sheath a Silastic tube of external diameter 4 mm.

Where rapid transfer of heat is required a thin metal sheath, e.g. aluminium foil, may be employed.

Although removal of the sheath from within the tubular product is preferably preceded by collapse of the sheath, the use of a thin sheath is also advantageous when it is to be removed by dissolution in a suitable solvent for the sheath (which solvent must obviously not undesirably affect the product).

Where a product is reshaped by the process of the present invention, the deformation step may be effected when the product is still "wet" with the liquid from which the fibres were spun or after removal of at least a proportion thereof, e.g. by evaporation or solvent extraction. Where the deforming step is effected while the product is still wet the liquid may be removed therefrom while the product is being subjected to the temperature/time cycle, conveniently by effecting the cycle at a sub-atmospheric pressure typically in the range of 1 to 5 mm of mercury.

Materials suitable for the preparation of products for use in the process of the present invention include polymeric substances and, in particular organic biologically acceptable polymeric substances. By biologically acceptable we mean substances that do not decompose or otherwise react undesirably when in contact with biological tissue with which they are likely to come into contact in use, for at least a useful period of time. As preferred substances we would mention fluorinated hydrocarbons, e.g. PTFE which conveniently may be spun from a dispersion of the material in a suitable dispersing agent, and polyurethanes which may be spun from solution, although other biologically acceptable polymers which can be electrostatically spun to give fibres are not excluded.

The fibrous products or at least some of the fibrous components of products for use in the present invention may be spun from a solution of or a dispersion of a polymer or its precursors. Polymers which may be conveniently spun from solution include high molecular weight fibre-forming thermoplastics; in particular we would mention polyurethane, polyamides and polyacrylonitrile. Polymers which may conveniently be spun from dispersion include polytetrafluoroethylene and polyesters.

As an example of a polymer precursor which may be spun from solution we mention urea formaldehyde which may be cross-linked subsequent to spinning by treatment with acid vapour.

Water soluble polymers, e.g. polyvinyl alcohol, polyvinyl pyrrolidone and polyethylene oxide, may be spun from aqueous solution. While we do not exclude the possibility that products prepared from such materials may be used as prepared, preferably such products are given at least a degree of insolubility in aqueous medium e.g. by cross-linking with a suitable reagent.

Where the products are spun from a dispersion the spinning material comprises preferably also a solution of an additional component which acts to enhance the viscosity of the suspension and to improve its fibre forming properties. Most convenient for this purpose, we have found, is an additional organic polymeric material which subsequent to fibre formation, can, if desired, be destroyed during sintering.

The preferred spinning material, then, is a solution or suspension which preferably comprises an organic polymer in an amount such that it is capable of forming a fibre and has cohesion properties such that the fibre form is retained during any post fibreization hardening until the fibre has hardened sufficiently not to lose its fibrous shape on detachment from a receiver where this is appropriate.

Where tubes are spun from solution they comprise point bonded fibres and are often strong enough for use without any further treatment.

Where products are spun from dispersion they often have a tendency to be friable, being mere agglomerations of discrete particles held together in the form of fibres by the additional organic polymeric component present. Preferably such products are sintered so that the particles soften and flow into each other and the fibres may become point bonded. In the case of PTFE sintering may conveniently be carried out between 330° C. and 450° C. preferably between 370° and 390° C. Sterilisation may proceed concurrently during the sintering process. The sintering temperature in the case of PTFE is usually sufficiently high to destroy completely any undesirable organic component in the final product, e.g. material added solely to enhance viscosity or emulsifying agent.

The additional organic component need be employed only in a relatively small proportion (usually within the range 0.001 to 12% and preferably 0.1 to 3%) by weight of the suspension, although the precise concentration of any particular application can easily be determined by trial.

The degree of polymerisation of the additional organic component is preferably greater than about 2000 units linearly; a wide range of such polymers is available. An important requirement is solubility of the polymer in the selected solvent or suspending medium which is preferably water. As examples of water-soluble polymeric compounds we may mention polyethylene oxide, polyacrylamide, polyvinyl pyrrolidone and polyvinyl alcohol; where an organic medium is employed to prepare the spinning material, either as the sole liquid solvent or as a component thereof, a further wide range of organic polymeric compounds is available, for example polystyrene and polymethylmethacrylate.

The degree of polymerisation of the polymer will be selected in the light of required solubility and the ability of the polymer to impart the desired properties of cohesion and viscosity to the fibreizable liquid.

We have found that generally the viscosity of the fibreizable liquid whether due solely to the presence of the fibreizable polymer or partly contributed to by the additional organic polymer should be greater than 0.1 but not greater than 150 poise. Preferably it is between 0.5 to 50 poise and more preferably between 1 and 10 poise, (viscosities being measured at low shear rates). The viscosity required using a given additional organic polymer will vary with the molecular weight of the polymer, i.e. the lower the molecular weight the higher the final viscosity needed. Again, as the molecular weight of the polymer is increased a lower concentration of it is required to give good fibreization. Thus, as examples we would mention that in the preparation of polytetrafluoroethylene products we have found that using polyethylene oxide of MW 100,000 as the additional organic polymer a concentration of about 12% by weight relative to the PTFE content is needed to give satisfactory fibreization, whereas with a MW of 300,000 a concentration of 1 to 6% may be adequate. Again, at a MW of 600,000 a concentration of 1 to 4% is satisfactory, while at a MW of $4 \times 10^6$ a concentration as low as 0.2% may give good fibreization.

The concentration of the fibreizable polymer will depend upon the amount required to provide adequate fibre properties, and will be influenced also by the need to produce a liquid of appropriate viscosity and speed of fibre hardening. Thus in the case of a dispersion we may use a concentration within the range 25% w/w to saturation (in the case of a dispersion, 'saturation' means the maximum concentration which may be included without destroying the useful spinnability of the liquid) preferably 40 to 70% and more preferably 50 to 60% and in the case of a solution we may use a concentration within the range 5 to 50% w/w, preferably 10 to 20% w/w.

It will be appreciated that the concentration of the components must each be adjusted to take account of the presence and concentration of any other and their relative effects upon viscosity etc.

The spinning material should have some electrical conductivity, although this may vary between quite wide limits; for example we prefer to employ solutions having conductivity within the range $1 \times 10^{-6}$ to $5 \times 10^{-2}$ mhos cm$^{-1}$.

Any convenient method may be employed to bring the spinning material into the electrostatic field, for example we have supplied the spinning liquid to an appropriate position in the electrostatic field by feeding it to a nozzle from which it is drawn by the field, whereupon fibreization occurs. Any suitable apparatus can be employed for this purpose; thus we have fed the spinning material from a syringe reservoir to the tip of an earthed syringe needle, the tip being located at an appropriate distance from an electrostatically charged surface. Upon leaving the needle the material forms fibre between the needle tip and the charged surface.

Droplets of the spinning liquid may be introduced into the field in other ways which will be apparent to the skilled man, the only requirement being that they can be held within the field at a distance from the electrostatically charged surface such that fibreization occurs. For example they could be carried into the field on, say, a continuous carrier, e.g. a metal wire.

It will be appreciated that where the liquid is fed into the field through a nozzle, several nozzles may be used to increase the rate of fibre production. Alternative means of bringing the fibreizable liquid into the charge field may be employed, for example a perforated plate (the perforations being fed with fibreizable liquid from a manifold) may be employed.

The electrostatic potential employed will usually be within the range 5 Kv to 1000 Kv, conveniently 10–100 Kv and preferably 10–50 Kv over a distance of 7–15 cm. Any appropriate method of producing the desired potential may be employed.

The optimum distance of the nozzle or other material supply means from the charged surface is determined quite simply by trial and error. We have found, for example that using a potential of the order of 20 Kv, a distance of 5–35 cm is suitable, but as the charge, nozzle dimensions, liquid flow rate, charged surface area etc. are varied so the optimum distance may vary, and it is most conveniently determined as described.

To allow high production rates, hardening of the fibres should occur rapidly and this is facilitated by the use of concentrated fibreizing liquids (so that the minimum liquid has to be removed), easily volatile solvents (for example the liquid may be wholly or partly of low boiling organic liquid) and relatively high temperatures in the vicinity of the fibre formation. The use of a gaseous, usually air, blast, particularly if the gas is warm, will often accelerate hardening of the fibre. Careful direction of the air blast may also be used to cause the fibres, after detachment, to lay in a desired position or direction.

Where dispersions are employed as the spinning material the particle size may be between 0.01 micron and 1 micron, preferably it is between 0.1 micron and 0.3 micron.

The as-spun fibrous surface usually has a porosity in the range 5% to 95% and the porosity will depend on the particular application; a typical porosity value is 75%. By the term porosity we mean the percentage of the total volume of the fibrous component of the product which is free space.

Tubes prepared according to the present invention may have walls between a few microns and a few centimeters thick, the choice of thickness will depend on the particular application and will be selected in the light of experience of the strength of the product after spinning and the conditions to which it will be exposed. However, we have found that when using polyurethane as the fibres the thickness of wall for use as a vascular graft will usually be within the range 5–25%, preferably 9-18%, and more preferably 10-12% of the internal diameter of the lumen. Spinning will usually, therefore be continued until a wall of desired thickness has been deposited, taking into consideration any dimensional changes which may result from shrinkage, e.g. on drying or cross-linking, or from elastic contraction of the fibres.

The pore size of the tubes prepared according to the invention will usually be between 0.001 micron and 500 micron. For the tube to be sufficiently porous to allow penetration of cells into the surface layers, preferably the average surface pore dimension should be of the order of 5 to 25 micron, particularly preferably between 7 and 15 micron, although pore size in the bulk of the material may average about 1 micron.

The products of the process of the present invention find wide application, particularly in the medical field, as tubular devices for use in suitable locations, for example as prostheses of various kinds, e.g. vascular and as synthetic urinary and bile ducts, as synthetic tracheae, and as tubes for a wide variety of other purposes. More particularly the said products are useful in providing components for the vascular circulatory system such as novel synthetic blood vessels or components thereof. Conveniently such synthetic vessels consist of tubes, preferably of circular cross-section, which may be of constant diameter along their length or may be of varying diameter or configuration, for example they may taper or they may include constrictions or grooves to facilitate their location. Such tubes may be of dimensions and configuration appropriate to the intended function and location in which they are to be employed, for example as a replacement for a diseased blood vessel, and they may, of course, be prepared upon a mandrel of corresponding dimensions and configurations.

Such synthetic vessels may be of the order of 0.1 to 3 cm, preferably 0.2 to 2 cm, and more preferably 0.3 to 0.8 cm in internal diameter. The thickness of the wall of the vessel may vary between wide limits, and will depend inter alia upon the strength and elasticity required in the tube as well as the need for it to be convenient to locate and affix. Usually the thickness of the vessel wall will be within the range 0.1 to 2 mm, preferably between 0.1 and 1 mm.

The synthetic vessel of the invention may be of any of a variety of configurations, for example it may be a straight or bent tube, a loop, an enastomosis or it may be bifurcate. Such forms may be obtained by spinning upon a former of suitable shape.

The preferred vessels comprise fibres of an appropriate polyurethane selected from the wide range of materials available on the basis of ease of fabrication, lack of toxicity, solubility, mechanical properties, degree of biodegradability, etc. While it is preferred that a completely polymerised polyurethane dissolved in a suitable solvent (together with other additives as required) is used as the spinning solution we do not exclude the possibility of spinning incompletely polymerised polyurethane, completion of polymerisation being effected during or after spinning.

Particular uses of synthetic blood vessels obtained by the process of the invention in animals including man include:

(a) arterio-venous shunts for use in renal dialysis,
(b) thin-walled prostheses for replacement of veins e.g. portal vein,
(c) construction of plumonary vessels in congenital heart malformation,
(d) replacement of small bore arteries (less than 8 mm internal diameter).

According to a further aspect of the invention, therefore, there is provided a product for use in medical or veterinary applications, particularly as a prosthesis for incorporation into a living organism, for example as a component of the vascular tree, prepared by the process hereinbefore described. Products made by the process are found to take sutures well, without undue tearing, and not to leak unduly upon slight puncture.

A further aspect of the invention provides a method for treating an animal including man which method comprises inserting a suitably dimensioned prosthetic device as hereinbefore described.

The invention is further illustrated in the attached drawings, in which.

The invention is further illustrated by the following examples.

EXAMPLE 1

A 15% solution of a polyether urethane block copolymer prepared from polytetrahydrofuran, butanediol and methylene-di-isocyanate (molar ratio 1:2.25:3.3) (having a hardness within the range 30°-40° Shore D) in DMF/MEK (3:2 w/w) was fed from a syringe into an electric field surrounding a cylindrical receiver of diameter 6 mm which was rotated about its long axis at about 300 rpm. Upon introduction of the copolymer droplets into the electric field they disintegrated into fibres which were drawn to the charged receiver (over a distance of 10 cm against a counter current of air at 40° C. moving at about 30 meters/min) and deposited upon it in a tubular layer. After allowing the layer to attain a thickness of about 0.75 mm the process was stopped and the receiver was removed from the fibrous tube (1).

Figure 4:
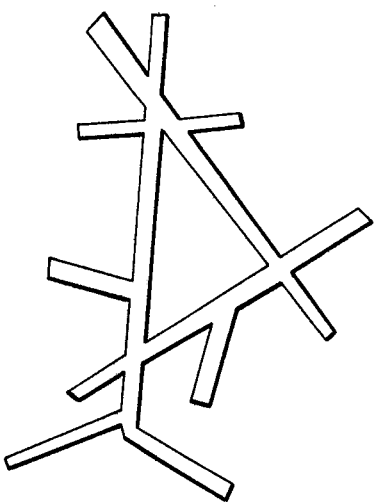
Figure 4B:
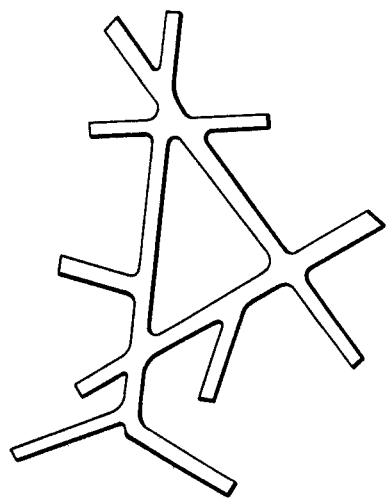
Figure 4C:
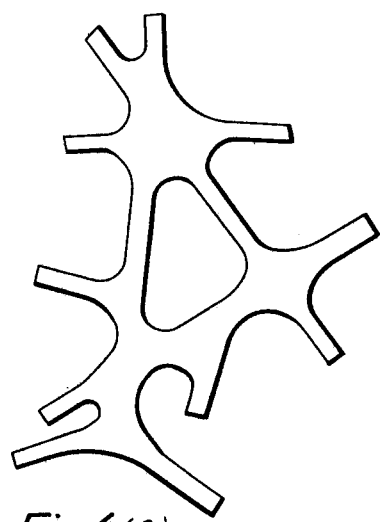

Samples of the spun tube were separately left in an oven at a range of temperatures and it was found, for example, that the sample maintained at a temperature of 80° C. for 24 hours retained its strength and elasticity, the sample maintained at a temperature of 105° C. for 16 hours was weaker and less elastic, the sample maintained at a temperature of 110° C. for 22 hours was appreciably weaker and less elastic, the sample maintained at a temperature of 120° C. for 12 hours was transparent, and the sample maintained at a temperature of 135° C. for 3 hours was transparent. The samples which had been maintained at 80° C., 105° C. and 110° C. were examined under a scanning electron microscope. FIG. 4 is a diagrammatic representation of the said heat treated samples as seen under the scanning electron microscope. From FIG. 4 it can be seen that after treatment at 80° C. the fibres inter-sect at well defined angles (FIG. 4a), after treatment at 105° C. the angles are becoming diffuse, i.e. the angularity of the sample is decreasing as the fibres start to flow and after treatment at 110° C. the angularity has been substantially lost as the fibres flow into each other at their intersections. Thus the melding temperature of the fibres was determined as approximately 105° C.

Samples of the spun tube were stretched to effect a strain therein of 20% i.e. the length of the tube was 120% of the length of the as-spun tube, the stretched samples were subjected to a range of temperature/time cycles, then released and the so-called recovery of the tubes was monitored. The results are given in Table 1.

TABLE 1

| Temp (°C.) | Time (hrs) | Immediate Recovery on release | Long term recovery |
|---|---|---|---|
| 105 | 16 | No recovery, i.e. 120% of as-spun length | No recovery; the tube was substantially weaker and had lost its elasticity |
| 80 | 4 | 110% of as-spun length | 106% of as-spun length |
| 80 | 8 | 115% of as-spun length | 112% of as-spun length |
| 80 | 18 | 118% of as-spun length | 118% of as-spun length |
| 80 | 24 | 119% of as-spun length | 119% of as-spun length |
| 80 | 36 | 119% of as-spun length | 119% of as-spun length |

It will be appreciated that where a tube is stretched to effect an "average" strain therein of x% and then deformed to form an arc of a circle the wall of the tube which forms the arc of the circle of smaller radius has a strain of less than x% and the wall of the tube which forms the arc of the circle of larger radius has a strain of more than x%.

A length of Silastic rubber tubing having an outer diameter of 4.5 mm was threaded through a sample of the electrostatically spun tube and a copper wire was then threaded through the lumen of the rubber tubing. The fibrous tube was streched until its length increased by 20%, its ends were clamped to the rubber tubing and to the copper wire, and it was bent to form an arc of a circle of diameter 2.5 cm. The fibrous tube, the rubber tubing and the copper wire were left in an oven at 80° C. for 24 hours. The fibrous tube was released and the rubber tubing and copper wire removed therefrom. On prolonged storage the reshaped fibrous tube showed substantially no recovery of its as-spun shape.

EXAMPLE 2

The spinning step of the process of Example 1 was repeated except that the charged receiver was a cylinder of diameter 4 mm instead of 6 mm and spinning was stopped when the fibrous layer had a thickness of 0.4 mm instead of 0.75 mm.

Figure 1:
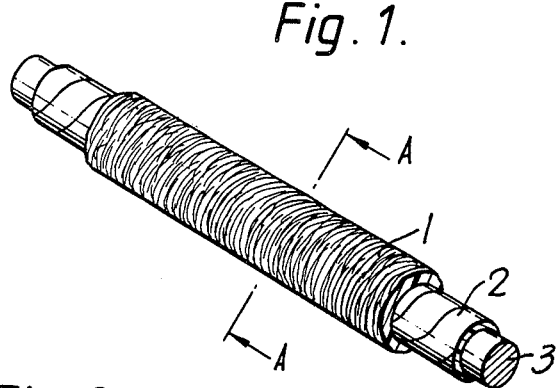
FIG. 1 is a perspective view of an electrostatically spun prosthesis mounted on a former consisting of a core and a sheath.
Figure 2:
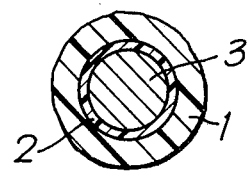
FIG. 2 is a cross-section on the line AA of FIG. 1.

A length of polyethylene helix (2) (Pliospire) having an outer diameter of 3 mm and an inner diameter of 1.5 mm was stretched and inserted in the fibrous tube (1). The helix was allowed to regain its original size and a copper wire (3) of diameter 1.6 mm was then threaded through it forcing it to expand (see FIGS. 1 and 2).

Figure 3:
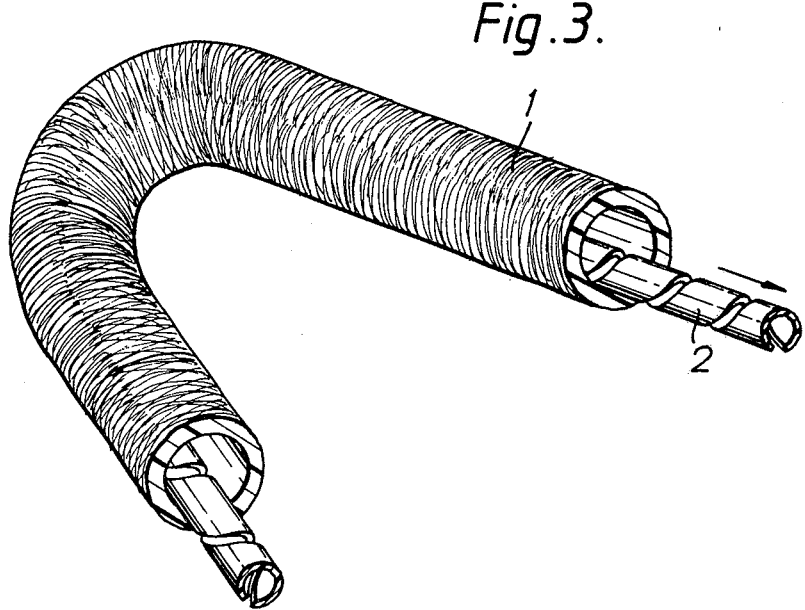
FIG. 3 shows diagrammatically the removal of the partially collapsed sheath from the lumen of the prosthesis after imparting a bend in the prosthesis.

The fibrous tube was stretched, its ends were clamped to the helix and to the wire, and it was bent into an arc of a circle of radius 2.5 cm. The tube, the helix and the wire were kept in a vac oven at 85° C. and 1 psi for 24 hours. They were allowed to cool to room temperature and the wire and then the helix were removed from the lumen of the fibrous tube (see FIG. 3). On prolonged storage the reshaped fibrous tube showed substantially no recovery of its as-spun shape.

Where the products of the present invention are to be employed in the medical field, particularly where they are employed as internal prostheses, they are preferably packaged in a suitable container, e.g. a plastics bag, and sterilised as part of the manufacturing process. Where sterilisation of the products is carried out it may be effected by radiation, heat treatment or chemical means.

Accordingly a further aspect of the invention provides a process for preparing a sterile product at least a portion of which comprises electrostatically spun fibres which process comprises setting the product in a desired shape as hereinbefore described, packaging the product in a suitable container and sterilising the product.

A further aspect of the invention provides a package comprising a sterile product prepared by a process as hereinbefore described in a suitable container.

What we claim is:

1. A process for stabilizing a product at least a portion of which comprises electrostatically spun fibres which process comprises the steps of holding the product under stress in a desired shape and/or size while the temperature thereof is maintained between the melding temperature of the said fibres and room temperature to set the product in the desired shape and/or size and then cooling the product or allowing it to cool.

2. A process as claimed in claim 1 wherein the product is deformed to give the desired shape.

3. A process as claimed in claim 1 wherein the temperature at which the product is maintained is between 80° C. and 20° C. below the melding temperature of the fibres.

4. A process as claimed in claim 1 wherein the product is released after cooling.

5. A process as claimed in claim 1 wherein the said temperature is maintained for between 12 and 48 hours.

6. A process as claimed in claim 1 wherein the said stress is sufficient to remove irregularities introduced into the product during the deformation step.

7. A process as claimed in claim 1 wherein the fibres are selected from a group of polymeric materials consisting of a fibre-forming polyurethane, fluorinated hydrocarbon, polyester, polyamide and polyacrylonitrile.

8. A process as claimed in claim 1 wherein the said portion is in the form of a tube, the electrostatically spun fibres comprise a polyurethane, and the said holding step is effected at a temperature in the range 75° to 90° C. for 24 to 36 hours.

9. A process as claimed in claim 1 or 6 wherein the said stress is a tensile stress.

10. A process as claimed in claim 9 wherein the said tensile stress generates a strain in the product of less than 25%.

11. A process as claimed in claim 1 wherein the said portion is in the form of a tube.

12. A process as claimed in claim 11 wherein the tubular portion has an internal diameter in the range 0.1 to 3.0 cm.

13. A process as claimed in claim 11 wherein the wall thickness of the tubular portion is in the range 0.1 to 2 mm.

14. A process as claimed in claim 1 wherein the product is mounted on a former.

15. A process as claimed in claim 14 wherein the product is attached to a former.

16. A process as claimed in claim 14 or 15 wherein the former has the desired shape before the product is mounted thereon.

17. A process as claimed in claim 14 or 15 wherein the former is given the desired shape after the product has been mounted thereon.

18. A process as claimed in claim 14 wherein the former consists of a core and a sheath therefor.

19. A process as claimed in claim 18 wherein the core is a substantially cylindrical mandrel.

20. A process as claimed in claim 19 wherein the mandrel is a metal rod or wire.

21. A process as claimed in claim 19 or 20 wherein the sheath comprises a rubbery or a thermoplastic material.

22. A process as claimed in claim 1 including the steps of packaging and sterilising the product.

23. A product for use in medical or veterinary applications prepared by the process of claim 1.

24. A package comprising a product as claimed in claim 23 in a suitable container.

* * * * *